United States Patent
Seino et al.

(10) Patent No.: US 12,428,400 B2
(45) Date of Patent: Sep. 30, 2025

(54) FLUORINE-CONTAINING FUSED RING PYRIMIDINE COMPOUND AND METHOD FOR PRODUCING SAME

(71) Applicant: UNIMATEC CO., LTD., Tokyo (JP)

(72) Inventors: Junya Seino, Kitaibaraki (JP); Rie Aotsu, Kitaibaraki (JP); Keisuke Kokin, Kitaibaraki (JP)

(73) Assignee: UNIMATEC CO., LTD. (JP)

( * ) Notice: Subject to any disclaimer, the term of this patent is extended or adjusted under 35 U.S.C. 154(b) by 511 days.

(21) Appl. No.: 17/925,449

(22) PCT Filed: Apr. 28, 2021

(86) PCT No.: PCT/JP2021/016976
§ 371 (c)(1),
(2) Date: Nov. 15, 2022

(87) PCT Pub. No.: WO2021/246095
PCT Pub. Date: Dec. 9, 2021

(65) Prior Publication Data
US 2023/0183211 A1 Jun. 15, 2023

(30) Foreign Application Priority Data
Jun. 1, 2020 (JP) .................. 2020-095719

(51) Int. Cl.
C07D 403/04 (2006.01)
(52) U.S. Cl.
CPC .................. C07D 403/04 (2013.01)
(58) Field of Classification Search
CPC .................................................... C07D 403/04
See application file for complete search history.

(56) References Cited

U.S. PATENT DOCUMENTS

2005/0261314 A1 11/2005 i Blasco et al.
2006/0281767 A1 12/2006 Gebauer et al.

FOREIGN PATENT DOCUMENTS

| CN | 1535113 A | 10/2004 |
|---|---|---|
| CN | 107286146 A | 10/2017 |
| CN | 108484508 A | 9/2018 |
| JP | S59-104364 A | 6/1984 |
| JP | 2010-065024 A | 3/2010 |
| JP | 2011-504931 A | 2/2011 |
| WO | 2010-018868 A1 | 2/2010 |

OTHER PUBLICATIONS

Saito et al., 19 Bioorg. & Med. Chem. 5955-5966 (2011) (Year: 2011).*
First Office Action issued in corresponding Chinese Patent Application No. 202180035236.7 dated Mar. 5, 2023, with English translation (13 Pages).
Li Ding et al., "Pharmacophores and Scaffolds are Dependent on Each Other for Their Tespective Effectiveness", Chapter 7: Drug Design Based on the Structure of Ligands, Mar. 31, 2018, pp. 174-175, with English translation.
Qian Xuhong, "Optimization of Lead Compounds", Dec. 31, 1994, pp. 120-121, with English translation.
Extended European Search Report issued in corresponding European Patent Application No. 21817578.4 dated May 22, 2024 (6 Pages).
Coxon, C.R. et al., "Cyclin-Dependent Kinase (CDK) Inhibitors: Structure-Activity Relationships and Insights into the CDK-2 Selectivity of 6-Substitute 2-Arylaminopurines", Journal of Medicinal Chemistry, vol. 60, 2017, pp. 1746-1767.
Saito, T. et al., "Pyrazolo[1,5-a]pyrimidines, Triazolo[1,5-a]pyrimidines and their Tricyclic Derivatives as Corticotropin-Releasing Factor 1 (CRF1) Receptor Antagonists", Bioorganic & Medicinal Chemistry, vol. 19, 2011, pp. 5955-5966.
Ghosh, I. et al., "Organic Semiconductor Photocatalyst Can Bifunctionalize Arenes and Heteroarenes", Science, vol. 365, 2011, pp. 360-366.
Donghai B.Y. et al., "Visible-Light Photoredox Decarboxylation of Perfluoroarene Iodine (III) Trifluoroacetates for C—H Trifluoromethylation of (Hetero)arenes", ACS Catalysis, vol. 8, 2018, pp. 2839-2843.
Ouyang, Y, et al., "Trifluoromethanesulfonic Anhydride as as Low-Cost and Versatile Trifluoromethylation Reagent", Angewandte Chemie International Edition, vol. 57, Issue 23, 2018, pp. 6926-6929.
International Search Report for corresponding International Application No. PCT/JP2021/016976 dated Jul. 6, 2021, with English translation (4 Pages).

(Continued)

Primary Examiner — Timothy R Rozof
(74) Attorney, Agent, or Firm — Harness, Dickey & Pierce, P.L.C.

(57) ABSTRACT

A fluorine-containing fused ring pyrimidine compound is provided represented by the following formula (1):

[Formula 1]

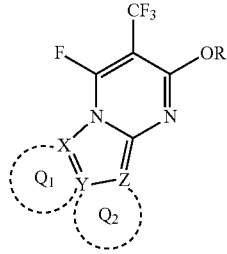

(1)

wherein in the above formula (1): R represents a hydrocarbon group having 1 to 12 carbon atoms; X, Y and Z each independently represent a carbon atom or a nitrogen atom; X and Y optionally form ring $Q_1$ with a carbon atom or a nitrogen atom bonded to each other; Y and Z optionally form ring $Q_2$ with a carbon atom or a nitrogen atom bonded to each other; and ring $Q_1$ and ring $Q_2$ each represent a monocyclic ring or fused ring having 6, 10 or 14 π electrons constituting the ring and optionally comprise a heteroatom.

6 Claims, No Drawings

(56) References Cited

OTHER PUBLICATIONS

Written Opinion for corresponding International Application No. PCT/JP2021/016976 dated Jul. 6, 2021, with English translation (6 Pages).
International Preliminary Report on Patentability for corresponding International Application No. PCT/JP2021/016976 dated Jul. 6, 2021, with English translation (7 Pages).
Coxon, C.R. et al., "Cyclin-Dependent Kinase (CDK) Inhibitors: Structure-Activity Relationships and Insights into the CDK-2 Selectivity of 6-Substitute 2-Arylaminopurines", Journal of Medicinal Chemistry, vol. 6, 2017, pp. 1746-1767.
Second Office Action issued in corresponding Chinese Patent Application No. 202180035236.7 dated Jul. 30, 2023, with English translation (8 Pages).
Office Action issued in corresponding Indian Patent Application No. 202237067277 dated Sep. 14, 2023, with English translation (6 Pages).

* cited by examiner

FLUORINE-CONTAINING FUSED RING PYRIMIDINE COMPOUND AND METHOD FOR PRODUCING SAME

CROSS REFERENCE TO RELATED APPLICATIONS

This is the National Stage of International Application No. PCT/JP2021/016976, filed Apr. 28, 2021, which claims the benefit of Japanese Patent Application No. 2020-095719 filed Jun. 1, 2020. The contents of these applications are incorporated hereby by reference in their entirety.

BACKGROUND

Technical Field

The present disclosure relates to a fluorine-containing fused ring pyrimidine compound and a method for producing the same.

Related Art

Conventionally, pyrimidine compounds have been reported to have various pharmacological activities, and among them, compounds with a heterocyclic ring fused to a pyrimidine ring, such as imidazopyrimidines, have gained attention. In particular, a compound having an imidazo[1,2-a]pyrimidine structure is expected to be used in the fields of medicine and agrochemicals.

More specifically, imidazo[1,2-a]pyrimidine having a substituent at the 4-position and 6-position of the pyrimidine ring has been investigated. Journal of Medicinal Chemistry, 2017, Vol. 60, pp. 1746-1767 reports that imidazo[1,2-a]pyrimidine exhibits an inhibitory activity on cyclin-dependent kinase 2 and discloses its investigation as anticancer pharmaceuticals. Bioorganic & Medicinal Chemistry, 2011, Vol. 19, pp. 5955-5966 reports imidazo[1,2-a]pyrimidine exhibiting an inhibitory activity on a corticotropin-releasing factor type 1 receptor and discloses investigation on the compound as a therapeutic agent for depression and anxiety disorders.

From such viewpoints, development of a fluorine-containing fused ring pyrimidine compound having not only substituents at the 4- and 6-positions of the pyrimidine ring but also a fluorine-containing substituent at the 5-position of the pyrimidine ring has drawn attention in anticipation of improvement in useful activities such as biological activity.

Meanwhile, as a method for introducing a trifluoromethyl group at the 5-position of a pyrimidine ring having substituents at the 4- and 6-positions, for example, the methods disclosed in Science, 2019, Vol. 365, pp. 360-366, ACS Catalysis, Vol. 8, 2018, pp. 2839-2843, Angewandte Chemie International Edition, Vol. 57, 2018, pp. 6926-6929, Chinese Patent Application Publication No. CN108484508A and Chinese Patent Application Publication No. CN107286146A have been known. Specifically, Science, 2019, Vol. 365, pp. 360-366 reports a method using sodium trifluoromethanesulfinate (Langlois reagent), ACS Catalysis, Vol. 8, 2018, pp. 2839-2843 reports a method using a trifluoroacetic acid derivative, and Angewandte Chemie International Edition, Vol. 57, 2018, pp. 6926-6929 reports a method using trifluoromethanesulfonic acid anhydride. Moreover, Chinese Patent Application Publication No. CN108484508A reports a method using trifluoroiodomethane and Chinese Patent Application Publication No. CN107286146A reports a method using trifluoromethyltrimethylsilane (Ruppert-Prakash reagent).

However, it has been conventionally difficult to produce a fluorine-containing fused ring pyrimidine compound having substituents at the 4- and 6-positions of the pyrimidine ring and a fluorine-containing substituent at the 5-position from the viewpoint of reactivity and selectivity, and such a fluorine-containing fused ring pyrimidine compound has not been reported. The fluorine-containing fused ring pyrimidine compound is expected to have various biological activities, and therefore a novel fluorine-containing fused ring pyrimidine compound having substituents at the 4- and 6-positions of a pyrimidine ring and a fluorine-containing substituent at the 5-position, and establishment of a production method therefor, have been desired.

The production methods reported in Science, 2019, Vol. 365, pp. 360-366, ACS Catalysis, Vol. 8, 2018, pp. 2839-2843, Angewandte Chemie International Edition, Vol. 57, 2018, pp. 6926-6929, and Chinese Patent Application Publication No. CN108484508A require light irradiation, which thereby may render scale-up difficult. Moreover, the production method of Science, 2019, Vol. 365, pp. 360-366 necessitates control of the oxygen concentration in the reaction mixture, and in the production method of ACS Catalysis, Vol. 8, 2018, pp. 2839-2843, pentafluoroiodobenzene to be reacted with the trifluoroacetic acid derivative is expensive, which thereby raises a concern of its management and operation complexity upon its reutilization. Furthermore, in the production method of Angewandte Chemie International Edition, Vol. 57, 2018, pp. 6926-6929, there may be problems such as the hygroscopicity of trifluoromethanesulfonic anhydride and the fuming and corrosiveness of trifluorosulfonic acid generated by moisture absorption.

Further, the production method of Chinese Patent Application Publication No. CN108484508A requires consideration of safety issues arising from the mutagenicity of trifluoroiodomethane. Furthermore, in the production method reported in Chinese Patent Application Publication No. CN107286146A, the Ruppert-Prakash reagent is expensive, which may render scale-up difficult and is considered to be unsuitable for practical use.

Then, the present inventors have found that reaction of a specific raw material enables a structure having a fluorine-containing substituent at the 5-position on the pyrimidine ring and substituted with prescribed substituents on the 4- and 6-positions to be easily established in a fused ring pyrimidine compound, and thus have completed the present disclosure.

SUMMARY

Namely, the present disclosure provides a novel fluorine-containing fused ring pyrimidine compound having substituents at the 4- and 6-positions of the pyrimidine ring and a fluorine-containing substituent at the 5-position, and a production method capable of easily producing the fluorine-containing fused ring pyrimidine compound.

The fluorine-containing fused ring pyrimidine compound according to an embodiment of the present disclosure is represented by the following formula (1):

[Formula 1]

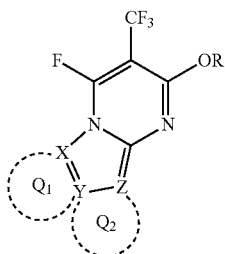

(1)

wherein
R represents a hydrocarbon group having 1 to 12 carbon atoms,
X, Y and Z each independently represent a carbon atom or a nitrogen atom,
X and Y optionally form ring $Q_1$ with a carbon atom or a nitrogen atom bonded to each other,
Y and Z optionally form ring $Q_2$ with a carbon atom or a nitrogen atom bonded to each other, and
ring $Q_1$ and ring $Q_2$ each represent a monocyclic ring or fused ring having 6, 10 or 14π electrons constituting the ring and optionally comprise a heteroatom.

The method for producing a fluorine-containing fused ring pyrimidine compound according to an embodiment of the present disclosure includes a step of reacting a fluoroisobutylene derivative represented by the following formula (2) with a compound represented by the following formula (3) or a salt thereof to obtain a fluorine-containing fused ring pyrimidine compound of the following formula (1):

[Formula 2]

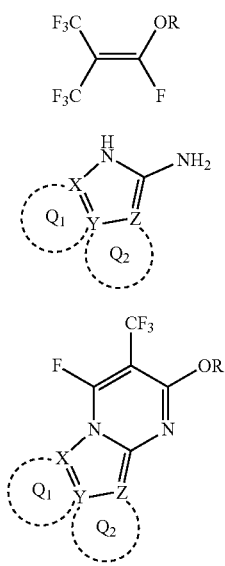

wherein
R represents a hydrocarbon group having 1 to 12 carbon atoms,
X, Y and Z each independently represent a carbon atom or a nitrogen atom,
X and Y optionally form ring $Q_1$ with a carbon atom or a nitrogen atom bonded to each other,
Y and Z optionally form ring $Q_2$ with a carbon atom or a nitrogen atom bonded to each other, and
ring $Q_1$ and ring $Q_2$ each represent a monocyclic ring or fused ring having 6, 10 or 14π electrons constituting the ring and optionally comprise a heteroatom.

The method for producing a fluorine-containing fused ring pyrimidine compound according to another embodiment of the present disclosure includes a step of reacting a fluoroisobutane derivative represented by the following formula (4) with a compound represented by the following formula (3) or a salt thereof to obtain a fluorine-containing fused ring pyrimidine compound of the following formula (1):

[Formula 3]

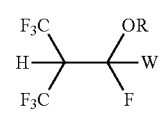

(4)

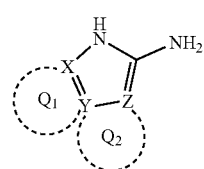

(3)

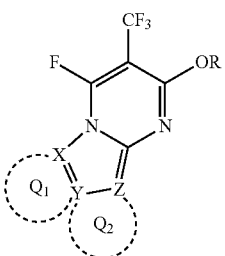

(1)

wherein
R represents a hydrocarbon group having 1 to 12 carbon atoms,
W represents a halogen atom, —OA$^1$, —SO$_m$A$^1$ where m is an integer of 0 to 3, or —NA$^1$A$^2$,
X, Y and Z each independently represent a carbon atom or a nitrogen atom,
X and Y optionally form ring $Q_1$ with a carbon atom or a nitrogen atom bonded to each other,
Y and Z optionally form ring $Q_2$ with a carbon atom or a nitrogen atom bonded to each other,
ring $Q_1$ and ring $Q_2$ each represent a monocyclic ring or fused ring having 6, 10 or 14π electrons constituting the ring and optionally comprise a heteroatom, and
A$^1$ and A$^2$ each independently represent a hydrogen atom or a hydrocarbon group having 1 to 10 carbon atoms.

In one embodiment of the present disclosure, R is an alkyl group having 1 to 10 carbon atoms.

Effects of Disclosure

According to the present disclosure, a novel fluorine-containing fused ring pyrimidine compound having substituents at the 4- and 6-positions of the pyrimidine ring and a fluorine-containing substituent at the 5-position, and a production method capable of easily producing the fluorine-containing fused ring pyrimidine compound, can be provided.

DETAILED DESCRIPTION

Hereinafter, embodiments of the present disclosure will be described in detail. However, the scope of the present disclosure is not limited to the specific examples described below.

(Fluorine-Containing Fused Ring Pyrimidine Compound)

The fluorine-containing fused ring pyrimidine compound in the present embodiment is represented by the following formula (1) and has the specific substituents (—OR, —CF$_3$, —F) at the 4-position, 5-position, and 6-position, respectively, on the pyrimidine ring. Furthermore, the fluorine-containing fused ring pyrimidine compound represented by formula (1) has a fused ring structure fused with a prescribed cyclic component, and specifically the cyclic component is fused together with one nitrogen atom on the pyrimidine ring and the carbon atom present between the two nitrogen atoms.

[Formula 4]

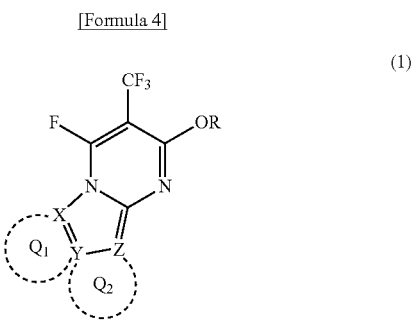

(1)

R is not particularly limited as long as it is a hydrocarbon group having 1 to 12 carbon atoms and is composed of a carbon atom and a hydrogen atom, and includes a chain hydrocarbon group, an aromatic hydrocarbon group, an alicyclic hydrocarbon group and the like. The chain hydrocarbon group is not particularly limited as long as the total number of carbon atoms is 1 to 12, and may be a linear hydrocarbon group or a branched chain hydrocarbon group. When R is an aromatic hydrocarbon group, the aromatic hydrocarbon group is not particularly limited as long as the total number of carbon atoms is 6 to 12, and may be an aromatic hydrocarbon group having a substituent or an aromatic hydrocarbon group having no substituent. Moreover, the aromatic hydrocarbon group may have a condensed polycyclic structure. When R is an alicyclic hydrocarbon group, the alicyclic hydrocarbon group is not particularly limited as long as the total number of carbon atoms is 3 to 12, and may be an alicyclic hydrocarbon group having a substituent or an alicyclic hydrocarbon group having no substituent. Further, the alicyclic hydrocarbon group may have a bridged ring structure.

Examples of the chain hydrocarbon group include alkyl groups such as a methyl group, an ethyl group, a n-propyl group, an i-propyl group, a n-butyl group, an i-butyl group, a sec-butyl group, a ter-butyl group, a pentyl group, a hexyl group, a heptyl group, an octyl group, a nonyl group, a decyl group, an undecyl group and a dodecyl group;

alkenyl groups such as an ethenyl group, a propenyl group, a butenyl group, a pentenyl group, a hexenyl group, a heptenyl group, an octenyl group, a nonenyl group, a decenyl group, an undecenyl group and a dodecenyl group; and alkynyl groups such as an ethynyl group, a propynyl group, a butynyl group, a pentynyl group, a hexynyl group, a heptynyl group, an octynyl group, a nonynyl group, a decynyl group, an undecynyl group and a dodecynyl group.

Examples of the aromatic hydrocarbon group include a phenyl group and a naphthyl group.

Examples of the alicyclic hydrocarbon group include a saturated or unsaturated cyclic hydrocarbon group, and examples of the cyclic hydrocarbon group include a cyclopropyl group, a cyclobutyl group, a cyclohexyl group, a cyclopentyl group, an adamantyl group and a norbornyl group.

R is preferably an alkyl group having 1 to 10 carbon atoms. R being an alkyl group having 1 to 10 carbon atoms enables the fluoroisobutylene derivative represented by formula (2) and the fluoroisobutane derivative represented by formula (4), which are raw materials for the fluorine-containing fused ring pyrimidine compound, to be easily prepared.

X, Y and Z each independently represent a carbon atom or a nitrogen atom. X and Y may also form ring $Q_1$ with a carbon atom or a nitrogen atom bonded to each other, and Y and Z may form ring $Q_2$ with a carbon or a nitrogen atom bonded to each other. When X and Y do not form ring $Q_1$ and Y and Z do not form ring $Q_2$, at least one of X, Y and Z is preferably a nitrogen atom. Moreover, in the case of X, Y and Z each being a carbon atom, each carbon atom optionally has a substituent. Examples of the substituents include an alkyl group having 1 to 10 carbon atoms, an aryl group having 1 to 10 carbon atoms, F, Cl, Br, I, $NO_2$, $CF_3$, CN, $NH_2$, OH and SH.

Ring $Q_1$ and ring $Q_2$ each represent a monocyclic ring or fused ring having 6, 10 or 14π-electrons constituting the ring. Here, the number of π-electrons refers to the number of π-electrons in the ring, and the monocyclic ring or the fused ring refers to a ring compound exhibiting aromaticity and having 6, 10 or 14π-electrons based on the Huckel rule. Examples of such a monocyclic ring and fused ring include benzene, naphthalene, azulene, anthracene and phenanthrene. Moreover, one or both of ring $Q_1$ and ring $Q_2$ may be a heterocyclic ring comprising a heteroatom. The heteroatom may be any of a nitrogen atom, an oxygen atom and a sulfur atom. The heterocyclic ring may also have any one of these heteroatoms, or may have a plurality of the same or different heteroatoms. In the case of one or both of ring $Q_1$ and ring $Q_2$ being a heterocyclic ring, such a heterocyclic ring includes furan, thiophene, pyrrole, pyridine, benzofuran, benzothiophene, indole, quinoline, and the like, and may be an isomer thereof. Among them, from the viewpoint of facilitating preparation of the compounds represented by formula (3) or salts thereof, which are raw materials for the fluorine-containing fused ring pyrimidine compound, one or both of ring $Q_1$ ring and ring $Q_2$ are preferably benzene, and either one thereof is more preferably benzene.

The fluorine-containing fused ring pyrimidine compound in the present embodiment has the specific substituents (—OR, —CF$_3$, —F) on the 4-position, 5-position and 6-position of the pyrimidine ring and thereby it can have an excellent effect from the viewpoint of structural expandability, and in particular desired biological activity (for example, inhibitory activity on various enzymes and cells and antibacterial activity against various bacteria) can be expected, and for example, control activity on pathogenic bacteria of rice blast and the like can be expected. Moreover, the substituents at the 4- and 6-positions of the pyrimidine ring being different groups (—OR and —F) facilitates derivatization into an asymmetric structure, and use as an intermediate can also be expected. More specifically, reacting the fluorine-containing fused ring pyrimidine compound under acidic conditions to modify —OR can provide a derivative. Moreover, reacting the fluorine-containing fused ring pyrimidine compound under basic conditions to modify —F can provide a derivative. Furthermore, the fluorine-containing fused ring pyrimidine compound in the present embodiment is also useful in the field of, for example, electronic materials such as organic semiconductors and liquid crystals.

(Method for Producing Fluorine-Containing Fused Ring Pyrimidine Compound)

The method for producing a fluorine-containing fused ring pyrimidine compound in the present embodiment includes (a) a step of reacting a fluoroisobutylene derivative represented by the following formula (2) with a compound represented by the following formula (3) or a salt thereof to obtain a fluorine-containing fused ring pyrimidine compound of the following formula (1):

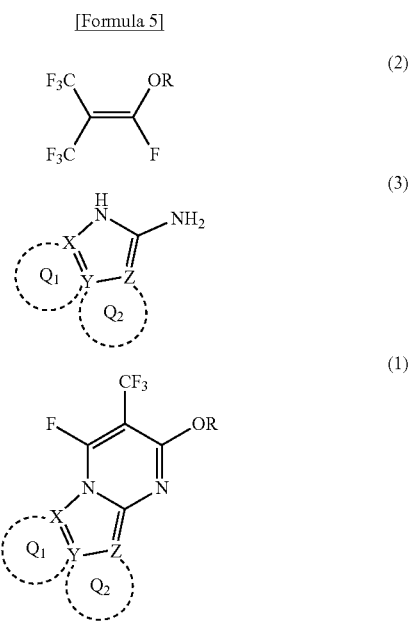

wherein in the above formulae (1) to (3),

R represents a hydrocarbon group having 1 to 12 carbon atoms,

X, Y and Z each independently represent a carbon atom or a nitrogen atom,

X and Y may form ring $Q_1$ with a carbon atom or a nitrogen atom bonded to each other, Y and Z may form ring $Q_2$ with a carbon atom or a nitrogen atom bonded to each other, and ring $Q_1$ and ring $Q_2$ each represent a monocyclic ring or fused ring having 6, 10 or $14\pi$ electrons constituting the ring and may comprise a heteroatom.

In formula (2), R is the same as that defined in the compounds of formula (1) described above, and in formula (3), each of X, Y, Z, ring $Q_1$ and ring $Q_2$ is the same as that defined in the compounds of formula (1) described above.

R in the above formula (2) is preferably an alkyl group having 1 to 10 carbon atoms. R in formula (2) can be, for example, an alkyl group having 1 to 10 carbon atoms in R defined in formula (1) described above.

A reaction of (a) above between the fluoroisobutylene derivative represented by formula (2) and the compound represented by formula (3) is represented by the following reaction formula (A).

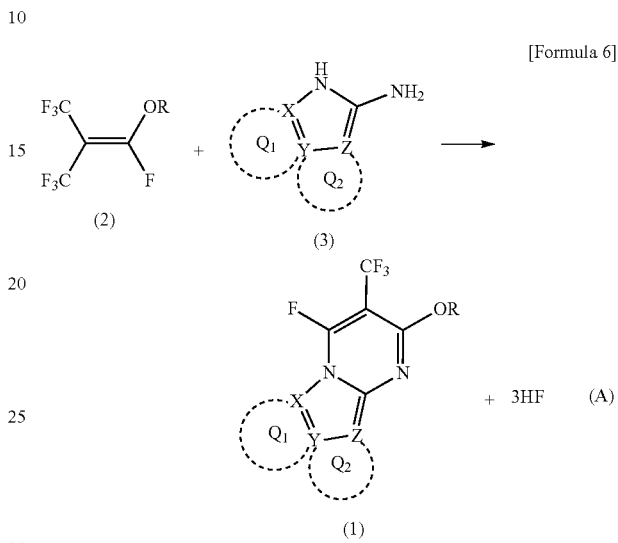

In the reaction formula (A), the compounds represented by formula (3) each may be in the form of salt. Examples of the compounds represented by formula (3) in the form of salts include a compound in a form of at least one of the moieties (—$NH_2$ and —NH—) constituting the amino group of the compounds represented by formula (3), being cationized to (—$NH_3^+$) and (—$NH_2^+$—) to form a salt with the counterion. The counterion is not particularly limited as long as it is a monovalent anion, and includes, for example, halide ions such as $F^-$, $Cl^-$, $Br^-$ and $I^-$.

In the method for producing a fluorine-containing fused ring pyrimidine compound in the present embodiment, for example, the reactions of (a) above can be carried out in one step in the presence of a hydrogen halide scavenger. Therefore, the fluorine-containing fused ring pyrimidine compounds represented by the above formula (1) can be easily obtained. In the reactions of (a) above, not only is a cyclic pyrimidine structure formed between the fluoroisobutylene derivative represented by formula (2) and the amino group of the compounds represented by formula (3), but also a cyclic component of the compounds represented by formula (3) is fused to the pyrimidine structure, resulting in synthesis of a fluorine-containing fused ring pyrimidine compound having the fused ring structure represented by formula (1). Further, —OR, $CF_3$ and F derived from the fluoroisobutylene derivative are located at the 4-position, 5-position and 6-position of the pyrimidine structure, respectively.

The hydrogen halide scavenger is a substance having a function of capturing hydrogen fluoride (HF) formed from a hydrogen atom derived from the amino group in the compounds represented by formula (3) and a fluorine atom derived from the fluoroisobutylene derivative represented by formula (2), in the reaction formula (A). As the hydrogen halide scavenger, an inorganic compound such as sodium hydroxide, potassium hydroxide, calcium hydroxide, sodium carbonate, potassium carbonate, sodium fluoride and potassium fluoride, an organic nitrogen derivative such as pyridine, triethylamine, diisopropylethylamine, diazabicyclononene, diazabicycloundecene, methyltriazabicyclodecene and diazabicyclooctane, and a phosphorus derivative such as a phosphazene base can be used.

The step of performing the reaction of (a) above to obtain a fluorine-containing fused ring pyrimidine compound may be carried out in the presence of a fluoride ion scavenger. The fluoroisobutylene derivative represented by the above formula (2) and the compound represented by the above formula (3) or a salt thereof are preferably reacted in the presence of, as a fluoride ion scavenger, a salt of a cation of lithium, sodium, magnesium, potassium, calcium or tetramethylammonium, and an anion of trifluoroacetic acid, heptafluorobutyric acid, methanesulfonic acid, ethanesulfonic acid, benzenesulfonic acid, toluenesulfonic acid, trifluoromethanesulfonic acid, nonafluorobutanesulfonic acid, bis(trifluoromethanesulfonyl)imide, bis(nonafluorobutanesulfonyl)imide, N,N-hexafluoropropane-1,3-disulfonyl imide, tetraphenylboric acid, tetrakis[3,5-bis(trifluoromethyl)phenyl]boric acid or tetrakis(pentafluorophenyl) boric acid. Among these, the potassium or sodium salt is preferably used, and the sodium salt is more preferably used. It is conjectured that the cation derived from the fluoride ion scavenger captures a fluoride ion isolated from the fluoroisobutylene derivative represented by formula (2) during the reaction, resulting in precipitation as a salt having low solubility in organic solvents, and thereby accelerating the reaction, which enables the fluorine-containing fused ring pyrimidine compound represented by formula (1) to be obtained in high yield.

A reaction temperature in reactions (a) above is preferably 0 to 100° C., more preferably 5 to 50° C., and still more preferably 10 to 20° C. A reaction time in reactions (a) above is preferably 0.5 to 48 hours, more preferably 1 to 36 hours, and still more preferably 2 to 12 hours.

A solvent used in the reactions of (a) above includes aprotic polar solvents such as tetrahydrofuran, monoglyme, diglyme, triglyme, tetraglyme, acetonitrile, dimethylformamide, dimethylacetamide, methylpyrrolidone, dimethylethyleneurea, tetramethylurea, dimethylsulfoxide and sulfolane, or two-phase solvents of a protonic polar solvent such as water and a water-insoluble solvent such as dichloromethane, toluene and diethyl ether. Moreover, as a catalyst for the reactions of (a) above, quaternary ammonium halides such as benzyltriethylammonium chloride, a quaternary phosphonium halide, crown ether, and the like can be optionally used.

A method for producing a fluorine-containing fused ring pyrimidine compound in another embodiment includes (b) a step of reacting a fluoroisobutane derivative represented by the following formula (4) with a compound represented by the following formula (3) or a salt thereof to obtain a fluorine-containing fused ring pyrimidine compound represented by the following formula (1):

[Formula 7]

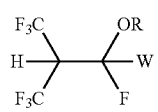

(4)

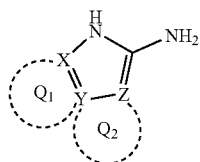

(3)

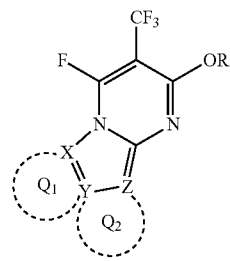

(1)

wherein in the above formula (1), (3) or (4)

R represents a hydrocarbon group having 1 to 12 carbon atoms,

W represents a halogen atom, $-OA^1$, $-SO_mA^1$ where m is an integer of 0 to 3, or $-NA^1A^2$, X, Y and Z each independently represent a carbon atom or a nitrogen atom, X and Y may form ring $Q_1$ with a carbon atom or a nitrogen atom bonded to each other, Y and Z may form ring $Q_2$ with a carbon atom or a nitrogen atom bonded to each other, ring $Q_1$ and ring $Q_2$ each represent a monocyclic ring or fused ring having 6, 10 or 14π electrons constituting the ring and may comprise a heteroatom, and $A^1$ and $A^2$ each independently represent a hydrogen atom or a hydrocarbon group having 1 to 10 carbon atoms.

In formula (4), R is the same as that defined in the compounds represented by formula (1) described above, and in formula (3), each of X, Y, Z, ring $Q_1$ and ring $Q_2$ is the same as that defined in the compounds represented by formula (1) described above.

In formula (4), R is preferably an alkyl group having 1 to 10 carbon atoms. R in formula (4) can be, for example, an alkyl group having 1 to 10 carbon atoms in R defined in the compound represented by formula (1) described above.

In W, the halogen atom is F, Cl, Br or I, with F or Cl being preferred.

In W, $A^1$ included in $-OA^1$ and $-SO_mA^1$ is a hydrogen atom or a hydrocarbon group having 1 to 10 carbon atoms. In the case of $A^1$ being a hydrocarbon group having 1 to 10 carbon atoms, for example, it can be a hydrocarbon group having 1 to 10 carbon atoms in R described above. In addition, m is an integer of 0 to 3, and preferably an integer of 0 to 1.

In W, $A^1$ and $A^2$ included in $-NA^1A^2$ are each independently a hydrogen atom or a hydrocarbon group having 1 to 10 carbon atoms. $A^1$ and $A^2$ may be the same or different from each other. When $A^1$ and $A^2$ are each a hydrocarbon group having 1 to 10 carbon atoms, for example, they can be hydrocarbon groups having 1 to 10 carbon atoms in R described above.

A reaction of (b) above between the fluoroisobutane derivative represented by formula (4) and the compound represented by formula (3) is represented by the following reaction formula (B).

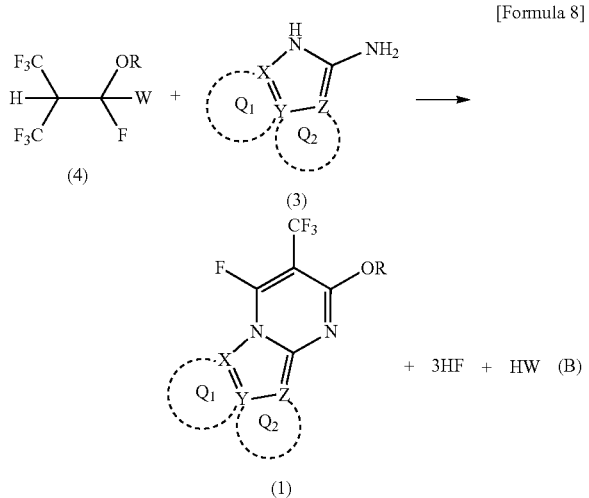

In the above reaction formula (B), the compounds represented by formula (3) each may be in the form of salts. Examples of the compounds represented by formula (3) in the form of salts include a compound in the form of at least one of the moieties (—$NH_2$ and —NH—) constituting the amino group of the compounds represented by formula (3), being cationized to (—$NH_3^+$) and (—$NH_2^+$—) to form a salt with the counterion. The counterion is not particularly limited as long as it is a monovalent anion, and includes, for example, halide ions such as $F^-$, $Cl^-$, $Br^-$ and $I^-$.

In the method for producing a fluorine-containing fused ring pyrimidine compound in the other embodiment, for example, the reactions of (b) above can be carried out in one step. Therefore, the fluorine-containing fused ring pyrimidine compounds represented by the above formula (1) can be easily obtained. In the reactions of (b) above, not only is a cyclic pyrimidine structure formed between the fluoroisobutane derivative represented by formula (4) and the amino group of the compounds represented by formula (3), but also the cyclic component of the compound represented by formula (3) is fused to the pyrimidine structure, resulting in synthesis of a fluorine-containing fused ring pyrimidine compound having the fused ring structure represented by formula (1). Further, —OR, $CF_3$ and F derived from the fluoroisobutane derivative are located at the 4-position, 5-position and 6-position of the pyrimidine structure, respectively.

A reaction temperature in reactions (b) above is preferably 0 to 100° C., more preferably 5 to 50° C., and still more preferably 10 to 20° C. A reaction time in reactions (b) above is preferably 0.5 to 48 hours, more preferably 1 to 36 hours, and still more preferably 4 to 24 hours. In the reactions of (b) above, the same hydrogen halide scavengers as those of (a) above may be used.

A solvent used in the reactions of (b) above includes aprotic polar solvents such as tetrahydrofuran, monoglyme, diglyme, triglyme, tetraglyme, acetonitrile, dimethylformamide, dimethylacetamide, methylpyrrolidone, dimethylethyleneurea, tetramethylurea, dimethylsulfoxide and sulfolane, or two-phase solvents of a protonic polar solvent such as water and a water-insoluble solvent such as dichloromethane, toluene and diethyl ether. Moreover, as a catalyst for the reactions of (b) above, quaternary ammonium halides such as benzyltriethylammonium chloride, a quaternary phosphonium halide and crown ether can be optionally used.

Although the embodiments of the present disclosure have been described above, the present disclosure is not limited to the aforementioned embodiments, and includes all aspects included in the concept and claims of the present disclosure, and can be variously modified within the scope of the present disclosure.

EXAMPLES

Hereinafter, Examples of the present disclosure will be described, but the present disclosure is not limited to these Examples as long as the gist of the present disclosure is not exceeded. Moreover, room temperature denotes a temperature within the range of 20° C.±5° C. unless otherwise specified.

Example 1

Production of 5-fluoro-7-methoxy-6-(trifluoromethyl)imidazo[1,2-a]pyrimidine

Under ice-water cooling, 1.0 g (3.8 mmol) of 2-aminoimidazole sulfate and 9.7 g (30 mmol) of potassium bis(trifluoromethanesulfonyl)imide were dissolved in 40 g of tetrahydrofuran, and 2.1 g (10 mmol) of 1,3,3,3-tetrafluoro-1-methoxy-2-(trifluoromethyl)-1-propene was added. Subsequently, a mixed solution of 5.0 g (39 mmol) of diisopropylethylamine and 10 g of tetrahydrofuran was added dropwise such that the internal temperature did not exceed 10° C., and the temperature was raised to room temperature. After about 16 hours, the contents underwent column purification to obtain 0.7 g of the compound represented by the following formula (5) (chemical formula: $C_8H_5F_4N_3O$, molecular weight: 235.14 g/mol). The isolated yield of the obtained compound was 39%.

[Formula 9]

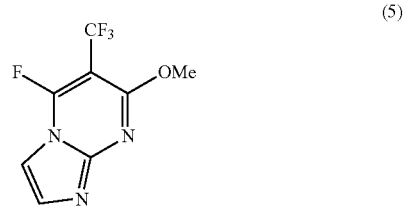

(5)

The analysis results were as follows.
Mass Spectrum (APCI, m/z): 235 ([M]$^+$)
$^1$H-NMR (400 MHz, $CDCl_3$) δ ppm: 7.68 (d, 1H), 7.06 (d, 1H), 3.78 (s, 3H)

Example 2

Production of 7-fluoro-5-methoxy-6-(trifluoromethyl)-[1,2,3]triazolo[1,2-a]pyrimidine Under ice-water cooling, 1.0 g (8.3 mmol) of 4-amino-1,2,3-triazole hydrochloride and 9.7 g (33 mmol) of potassium bis(trifluoromethanesulfonyl)imide were dissolved in 40 g of tetrahydrofuran, and 2.1 g (10 mmol) of 1,3,3,3-tetrafluoro-1-methoxy-2-(trifluoromethyl)-1-propene was added. Subsequently, a mixed solution of 5.6 g (43 mmol) of diisopropylethylamine and 10 g of tetrahydrofuran was added dropwise such that the internal temperature did not exceed 10° C., and the temperature was raised to room temperature. After about 16 hours, the contents underwent column purification to obtain 0.5 g of the compound represented by the following formula (6) (chemical formula: $C_7H_5F_4N_4O$, molecular weight: 236.13 g/mol). The isolated yield of the obtained compound was 25%.

[Formula 10]

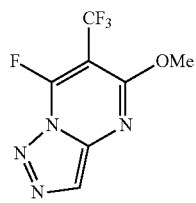

(6)

The analysis results were as follows.
Mass Spectrum (APCI, m/z): 236 ($[M]^+$)
$^1$H-NMR (400 MHz, CDCl$_3$) δ ppm: 7.52 (s, 1H), 3.79 (s, 3H)

Example 3

Production of 4-fluoro-2-methoxy-3-(trifluoromethyl)pyrimido[2,1-a]isoindole

Under ice-water cooling, 1.0 g (6.0 mmol) of 1H-isoindole-3-amine hydrochloride was dissolved in 50 g of tetrahydrofuran, and 1.3 g (6 mmol) of 1,3,3,3-tetrafluoro-1-methoxy-2-(trifluoromethyl)-1-propene was added. Subsequently, a mixed solution of 5.0 g (39 mmol) of diisopropylethylamine and 10 g of tetrahydrofuran was added dropwise such that the internal temperature did not exceed 10° C., and the temperature was raised to room temperature. After about 16 hours, the contents underwent column purification to obtain an intermediate. 0.4 g (1.2 mmol) of the obtained intermediate was dissolved in 10 g of tetrahydrofuran under refrigerant cooling, and 0.8 g (2.4 mmol) of potassium bis(trifluoromethanesulfonyl)imide was added. Subsequently, 5 g of a tetrahydrofuran solution containing 1.0 g (3.1 mmol) of tert-butylimino-tri(pyrrolidino)phosphorane was added dropwise such that the internal temperature did not exceed 10° C. After about 10 hours, the contents underwent column purification to obtain 90 mg of the compound represented by the following formula (7) (chemical formula: $C_{13}H_8F_4N_2O$, molecular weight: 284.21 g/mol). The isolated yield of the obtained compound was 5%.

[Formula 11]

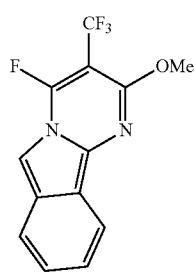

(7)

The analysis results were as follows.
Mass Spectrum (APCI, m/z): 284 ($[M]^+$)
$^1$H-NMR (400 MHz, CDCl$_3$) δ ppm: 7.55 (m, 3H), 7.35 (m, 2H), 3.65 (s, 3H)

Example 4

Production of 4-fluoro-2-methoxy-3-(trifluoromethyl)benzo[4,5]imidazo[1,2-a]pyrimidine Under ice-water cooling, 1.0 g (4.0 mmol) of 2-aminobenzimidazole trifluoroacetate and 5.1 g (16 mmol) of potassium bis(trifluoromethanesulfonyl)imide were dissolved in 40 g of tetrahydrofuran, and 1.0 g (4.6 mmol) of 1,3,3,3-tetrafluoro-1-methoxy-2-(trifluoromethyl)-1-propene was added. Subsequently, a mixed solution of 2.7 g (21 mmol) of diisopropylethylamine and 10 g of tetrahydrofuran was added dropwise such that the internal temperature did not exceed 10° C., and the temperature was raised to room temperature. After about 16 hours, the contents underwent column purification to obtain 0.2 g of the compound represented by the following formula (8) (chemical formula: $C_{12}H_7F_4N_3O$, molecular weight: 285.20 g/mol). The isolated yield of the obtained compound was 18%.

[Formula 12]

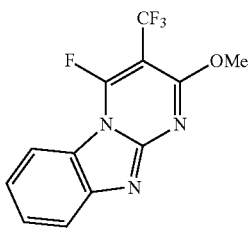

(8)

The analysis results were as follows.
Mass Spectrum (APCI, m/z): 285 ($[M]^+$)
$^1$H-NMR (400 MHz, CDCl$_3$) δ ppm: 8.68 (m, 2H), 7.57 (m, 2H), 4.07 (s, 3H)

Example 5

Production of 5-fluoro-7-methoxy-6-(trifluoromethyl)imidazo[1,2-a]pyrimidine by Using 1,1,1,3,3-pentafluoro-3-methoxy-2-(trifluoromethyl)-propane instead of 1,3,3,3-tetrafluoro-1-methoxy-2-(trifluoromethyl)-1-propene in Example 1

Under ice-water cooling, 1.0 g (3.8 mmol) of 2-aminoimidazole sulfate and 12 g (38 mmol) of potassium bis(trifluoromethanesulfonyl)imide were dissolved in 40 g of tetrahydrofuran, and 2.3 g (10 mmol) of 1,1,1,3,3-pentafluoro-3-methoxy-2-(trifluoromethyl)-propane was added. Subsequently, a mixed solution of 6.4 g (49 mmol) of diisopropylethylamine and 10 g of tetrahydrofuran was added dropwise such that the internal temperature did not exceed 10° C., and the temperature was raised to room temperature. After about 16 hours, the contents underwent column purification. The analysis results of the obtained compound were the same as those of the product of Example 1.

Example 6

Production of 7-fluoro-5-methoxy-6-(trifluoromethyl)-[1,2,3]triazolo[1,2-a]pyrimidine by Using 1,1,1,3,3-pentafluoro-3-methoxy-2-(trifluoromethyl)-propane Instead of 1,3,3,3-tetrafluoro-1-methoxy-2-(trifluoromethyl)-1-propene in Example 2

Under ice-water cooling, 1.0 g (8.3 mmol) of 4-amino-1,2,3-triazole hydrochloride and 13 g (42 mmol) of potassium bis(trifluoromethanesulfonyl)imide were dissolved in 40 g of tetrahydrofuran, and 2.3 g (10 mmol) of 1,1,1,3,3-pentafluoro-3-methoxy-2-(trifluoromethyl)-propane was added. Subsequently, a mixed solution of 7.0 g (54 mmol) of diisopropylethylamine and 10 g of tetrahydrofuran was added dropwise such that the internal temperature did not exceed 10° C., and the temperature was raised to room temperature. After about 16 hours, the contents underwent column purification. The analysis results of the obtained compound were the same as those of the product of Example 2.

Example 7

Production of 4-fluoro-2-methoxy-3-(trifluoromethyl)benzo[4,5]imidazo[1,2-a]pyrimidine by Using 1,1,1,3,3-pentafluoro-3-methoxy-2-(trifluoromethyl)-propane Instead of 1,3,3,3-tetrafluoro-1-methoxy-2-(trifluoromethyl)-1-propene in Example 4

Under ice-water cooling, 1.0 g (4.0 mmol) of 2-aminobenzimidazole trifluoroacetate and 6.4 g (20 mmol) of potassium bis(trifluoromethanesulfonyl)imide were dissolved in 40 g of tetrahydrofuran, and 1.1 g (4.6 mmol) of 1,1,1,3,3-pentafluoro-3-methoxy-2-(trifluoromethyl)-propane was added. Subsequently, a mixed solution of 3.4 g (26 mmol) of diisopropylethylamine and 10 g of tetrahydrofuran was added dropwise such that the internal temperature did not exceed 10° C., and the temperature was raised to room temperature. After about 16 hours, the contents underwent column purification. The analysis results of the obtained compound were the same as those of the product of Example 4.

In Examples 5 to 7, the isolated yields of the obtained compounds were not calculated, but types and amounts of impurities are expected to be increased due to byproducts that can be generated in the course of producing 1,3,3,3-tetrafluoro-1-methoxy-2-(trifluoromethyl)-1-propene from 1,1,1,3,3-pentafluoro-3-methoxy-2-(trifluoromethyl)-propane in the reaction system. Therefore, the production methods of Examples 1, 2 and 4 are conjectured to give high isolated yields of the obtained products as compared with the corresponding production methods of Examples 5, 6 and 7.

Test Example of Biological Activity

Evaluation Test for Rice Blast 4-fluoro-2-methoxy-3-(trifluoromethyl)benzo[4,5]imidazo[1,2-a]pyrimidine prepared in Example 4 was dissolved in acetone to prepare a solution having a concentration of 100,000 ppm. Next, to 1 ml of this acetone solution was added sterilized water up to 50 ml to prepare a test solution having a concentration of 2,000 ppm. Moreover, to 10 ml of a test solution having a concentration of 2,000 ppm prepared separately was added sterilized water up to 20 ml to prepare a test solution having a concentration of 1,000 ppm. 1,000 µl of the test solution having a concentration of 2,000 ppm and the test solution having a concentration of 1,000 ppm were each added dropwise to a separately fabricated oatmeal culture medium, and air-dried. Subsequently, a rice blast disc having a diameter of 8 mm was placed such that flora contacted a treated surface of the oatmeal culture medium. Then, the oatmeal culture medium was allowed to stand still in a thermostatic room at 25° C. for 7 days, and an elongation length of hyphae was then investigated. The results are shown in Table 1. The control value was calculated according to the following expression. In the following expression, "without treatment" means that 1 ml of acetone was diluted with sterilized water to 50 ml as a test solution, and the solution was added dropwise to the culture medium. In addition, "with treatment" means that a test solution that had been diluted and adjusted to a set concentration was added dropwise to the culture medium.

TABLE 1

| Concentration of test solution (ppm) | Control value |
|---|---|
| 2000 | 96 |
| 1000 | 66 |

Control value={(average of elongation lengths of hyphae without treatment−average of elongation lengths of hyphae with treatment)/average of elongation lengths of hyphae without treatment}×100     [Expression 1]

As shown in Table 1, the fluorine-containing fused ring pyrimidine compound of the present disclosure exhibits the control activity against the pathogens of rice blast and is found to be effective as a compound exhibiting a biological activity.

The invention claimed is:
1. A fluorine-containing fused ring pyrimidine compound represented by the following formula (1):

[Formula 1]

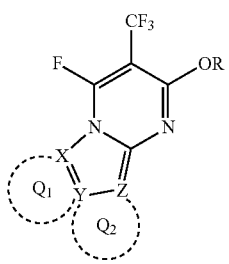

(1)

wherein
R represents a hydrocarbon group having 1 to 12 carbon atoms,
X, Y and Z each independently represent a carbon atom or a nitrogen atom,
X and Y optionally form ring $Q_1$ with a carbon atom or a nitrogen atom bonded to each other,
Y and Z optionally form ring $Q_2$ with a carbon atom or a nitrogen atom bonded to each other, and ring $Q_1$ and ring $Q_2$ each represent a monocyclic ring or fused ring having 6, 10 or 14π electrons constituting the ring and optionally comprise a heteroatom.

2. The fluorine-containing fused ring pyrimidine compound according to claim 1, wherein R is an alkyl group having 1 to 10 carbon atoms.

3. A method for producing a fluorine-containing fused ring pyrimidine compound, comprising:
a step of reacting a fluoroisobutylene derivative represented by the following formula (2) with a compound represented by the following formula (3) or a salt thereof to obtain a fluorine-containing fused ring pyrimidine compound of the following formula (1):

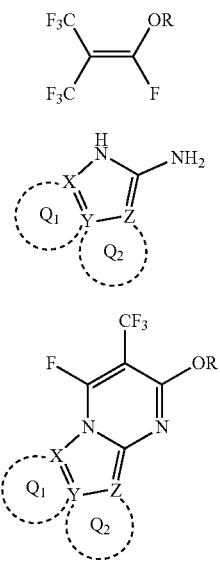

wherein
R represents a hydrocarbon group having 1 to 12 carbon atoms,
X, Y and Z each independently represent a carbon atom or a nitrogen atom,
X and Y optionally form ring $Q_1$ with a carbon atom or a nitrogen atom bonded to each other,
Y and Z optionally form ring $Q_2$ with a carbon atom or a nitrogen atom bonded to each other, and
ring $Q_1$ and ring $Q_2$ each represent a monocyclic ring or fused ring having 6, 10 or 14π electrons constituting the ring and optionally comprise a heteroatom.

4. A method for producing a fluorine-containing fused ring pyrimidine compound, comprising:
a step of reacting a fluoroisobutane derivative represented by the following formula (4) with a compound represented by the following formula (3) or a salt thereof to obtain a fluorine-containing fused ring pyrimidine compound of the following formula (1):

[Formula 3]

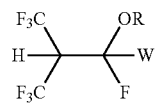

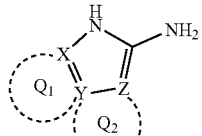

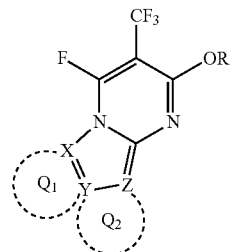

wherein
R represents a hydrocarbon group having 1 to 12 carbon atoms,
W represents a halogen atom, —$OA^1$, —$SO_mA^1$ where m is an integer of 0 to 3, or —$NA^1A^2$,
X, Y and Z each independently represent a carbon atom or a nitrogen atom,
X and Y optionally form ring $Q_1$ with a carbon atom or a nitrogen atom bonded to each other,
Y and Z optionally form ring $Q_2$ with a carbon atom or a nitrogen atom bonded to each other,
ring $Q_1$ and ring $Q_2$ each represent a monocyclic ring or fused ring having 6, 10 or 14π electrons constituting the ring and optionally comprise a heteroatom, and
$A^1$ and $A^2$ each independently represent a hydrogen atom or a hydrocarbon group having 1 to 10 carbon atoms.

5. The method for producing a fluorine-containing fused ring pyrimidine compound according to claim 3, wherein R is an alkyl group having 1 to 10 carbon atoms.

6. The method for producing a fluorine-containing fused ring pyrimidine compound according to claim 4, wherein R is an alkyl group having 1 to 10 carbon atoms.

* * * * *